United States Patent [19]

Pelikan et al.

[11] Patent Number: 5,680,857

[45] Date of Patent: Oct. 28, 1997

[54] ALIGNMENT GUIDE SYSTEM FOR TRANSMISSIVE PULSE OXIMETRY SENSORS

[75] Inventors: Glenn L. Pelikan, Multnomah, Oreg.; Hodjat Habibi, Snohomish; Robert Hartwig, Pierce, both of Wash.

[73] Assignee: SpaceLabs Medical, Inc., Redmond, Wash.

[21] Appl. No.: 937,248

[22] Filed: Aug. 28, 1992

[51] Int. Cl.⁶ ..................................... A61B 5/00
[52] U.S. Cl. ..................... 128/633; 128/665; 356/152
[58] Field of Search ........................... 128/633, 634, 128/664–7; 356/41, 39, 40, 152

[56] References Cited

U.S. PATENT DOCUMENTS

| | | | |
|---|---|---|---|
| 3,938,895 | 2/1976 | Bridger et al. | 356/152 |
| 4,865,038 | 9/1989 | Rich et al. | 128/665 X |
| 5,005,573 | 4/1991 | Buchanan | 128/207.14 |
| 5,040,539 | 8/1991 | Schmitt et al. | 128/633 |
| 5,080,098 | 1/1992 | Willett et al. | 128/665 X |

FOREIGN PATENT DOCUMENTS

| | | |
|---|---|---|
| 0 127 947 | 12/1984 | European Pat. Off. . |
| 0 315 040 | 5/1989 | European Pat. Off. . |

*Primary Examiner*—John P. Lacyk
*Attorney, Agent, or Firm*—Seed and Berry LLP

[57] ABSTRACT

An alignment guide system for use with conventional pulse oximetry monitors connected to transmissive pulse oximetry sensors. The system generates a bar graph or other display showing the magnitude of the optical coupling between the LED's and light detector used in the sensor. By manipulating the position of the sensor while observing the bar graph, medical practitioners can optimize the mount of light from the LED's reaching the light detector. The bar graph also contains an alarm limit marker. If the bar graph falls below the alarm limit marker, the entire bar graph flashes to alert the medical practitioner that the mount of light transmitted to the LED's to the light detector may not be enough to permit sufficiently accurate oxygen saturation measurements.

14 Claims, 5 Drawing Sheets

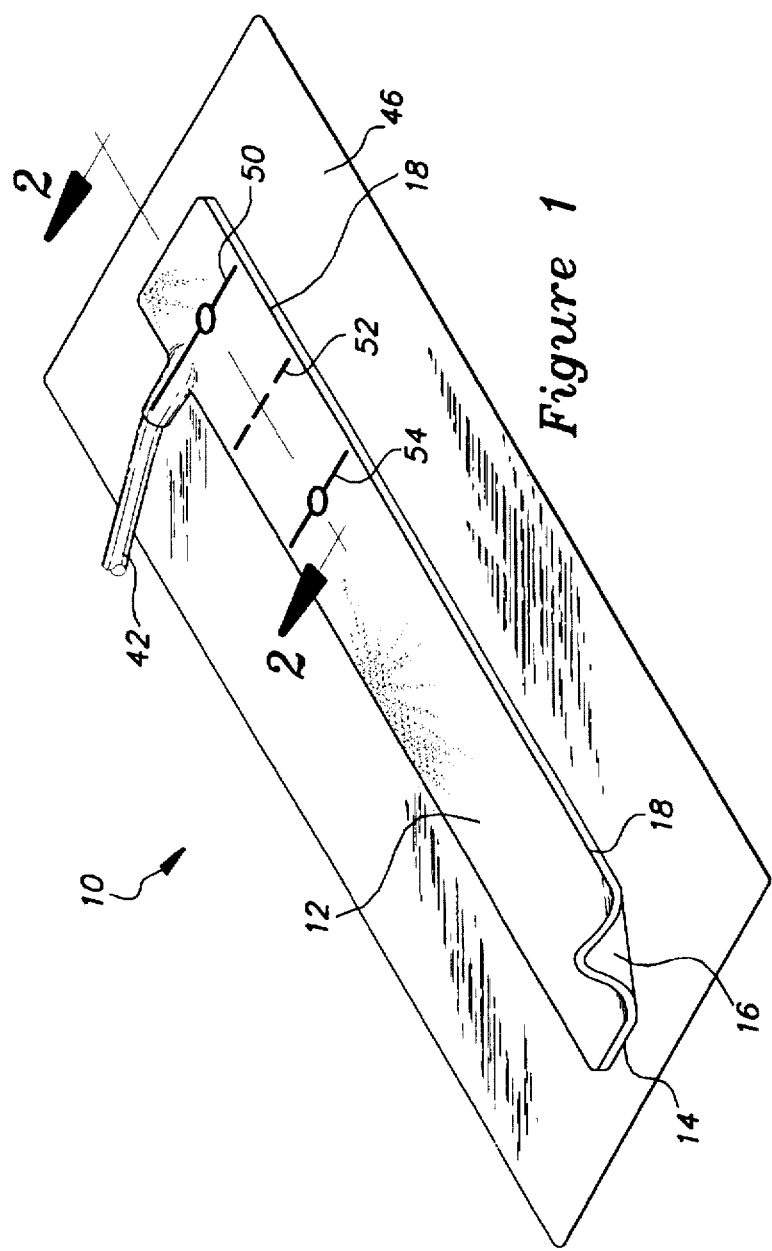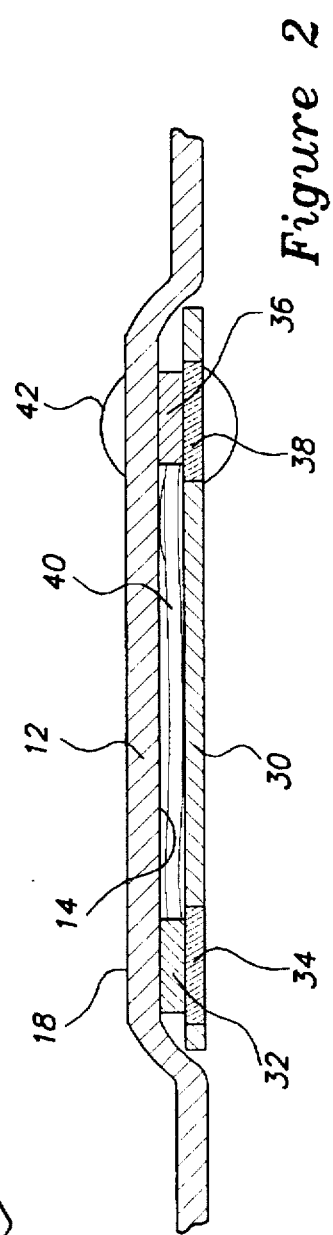

ALIGNMENT GUIDE SYSTEM FOR TRANSMISSIVE PULSE OXIMETRY SENSORS

TECHNICAL FIELD

This invention relates to pulse oximeters, and more particularly, to pulse oximeters used with light transmissive pulse oximetry sensors.

BACKGROUND OF THE INVENTION

Pulse oximeters are in common use in hospitals and other medical facilities to measure the degree of oxygen saturation of a patient's blood. Conventional pulse oximeters typically operate according to the Lambert-Beers law which is based upon the blood's property of differentially absorbing infrared and red light depending upon the degree of oxygen saturation of the patient's blood.

Conventional pulse oximeters typically consist of a pulse oximetry sensor connected to a pulse oximetry monitor. The monitor typically includes circuitry for interfacing with the sensor as well as a display for providing a readout of the percent of oxygen saturation. The sensor typically contains a first light emitting diode ("LED") emitting red light, a second LED emitting infra-red light, and a light detector for sensing the red and infra-red light after passing through vascularized tissues of the patient. The first and second LED's are normally time multiplexed by alternately applying illumination signals to the LED's so that a single light detector can be used.

There are two types of pulse oximetry sensors in present use, namely "reflectance sensors" and "transmissive sensors". In a reflectance sensor, the LED's and light detector are mounted adjacent each other on a single carder. The carder is placed against the skin of a patient so that Light from the LED's passes into the tissues of the patient, and some of this light is internally reflected back to the light detector. The magnitude of the reflected light is an inverse function of the mount of light absorbed in the tissues. The differential reflection of red and infra-red light thus provides an indication of the degree of oxygen saturation in the tissues.

In transmissive pulse oximetry sensors, the LED's are mounted adjacent to each other in a first carrier, and the light detector is mounted in either a second carrier or in a separate portion of the first carrier. As a result, the LED's and the light detector can be placed on opposite surfaces of vascularized tissues, such as a finger or an ear lobe, with the LED's and the light detector facing each other. Light from the LED's is transmitted through the tissues to the light detector. The magnitude of the light transmitted to the light detector is an inverse function of the amount of light absorbed in the tissues. The differential transmission of red and infra-red light thus provides an indication of the degree of oxygen saturation in the tissues.

The geometry between the LED's and the light detector can be critical to the optimum performance of pulse oximeters. Ideally, the optical paths between the LED's and the light detector are as short as possible to maximize the usable light reaching the light detector. However, if the LED's and/or the light detector are either not in the proper position or not facing the proper direction, the accuracy of the oxygen saturation measurement can be degraded.

The geometry between the LED's and the light detector in a reflectance sensor is fixed because the LED's and light detector are mounted on the same carrier. Thus, variations in the geometry between the LED's and the light detector is not a problem for reflectance sensors. Similarly, the geometry between the LED's and the light detector in many transmissive sensors is also fixed because the first and second carriers are pivotally connected to each other. Variations in the geometry between the LED's and the light detector is also not a problem for these types of transmissive sensors.

One commonly used transmissive pulse oximetry sensor uses as the carrier an elongated flexible web having one of its surfaces coated with an adhesive in a manner similar to a bandage strip. The LED's are mounted in or on the web adjacent to each other, and the light detector is mounted in or on the web at a location that is longitudinally spaced from the LED's. The sensor is generally used by wrapping the web around a finger or a portion of a hand or foot so that the LED's are directly opposite the light detector.

In practice, pulse oximetry sensors having LED's and a light detector mounted on a common flexible web are often applied improperly so that the LED's are either not directly opposite the light detector or not directly facing the light detector. Three types of alignment errors can occur either alone or in combination. In the first, the web is attached to the patient so that the LED's are laterally offset from the light detector. For example, the LED's will be laterally offset from the light detector if the web is wrapped around a finger in a spiral. In the second type of alignment error, the web is attached to the patient so that the LED's are longitudinally offset from the light detector. An example of this condition is where the web is wrapped around a finger, but one-half the circumference of the finger is not substantially the same distance as the spacing between the LED's and the light detector. Finally, the third type of alignment error occurs if the LED's do not directly face the light detector even though they may be positioned directly opposite the light detector. This type of alignment error may occur if the opposite surfaces of the skin to which the LED's and light detector are attached are not parallel to each other.

As mentioned above, these three types of alignment errors can occur either alone or in combination. The possibility of three different types of alignment errors occurring coupled with inevitable variations in the size and shape of attachment locations among patients and variations in the training and skill of medical personnel attaching sensors, often hurriedly in emergency conditions, makes it very difficult to be sure that sensors are attached properly to provide accurate oxygen saturation measurements.

Although manufacturers of pulse oximetry sensors having LED's and a light detector mounted on a common web have recognized the importance of properly aligning the LED's with the light detector, they have been unable to devise any suitable technique to quickly and accurately ensure optimum alignment between the LED's and the light detector. One approach has been to place alignment marks on the exposed surface of the web over the LED's and the light detector. These alignment marks are in the form of respective lines extending laterally across the web over the LED's and light detector. In theory, the medical practitioner can make sure that the alignment marks are opposite each other to ensure that the LED's are properly aligned with the light detector. However, this approach has often proven to be inadequate for several reasons. First, the alignment marks are often covered up by portions of the web extending beyond the LED's and light detector which are wrapped around the portion of the web containing the alignment marks. Second, it is sometimes difficult to determine if the marks are, in fact, directly opposite each other even when the marks are clearly visible. Third, even if the marks are, in fact, longitudinally and laterally aligned with each other, the LED's may still not be directly facing the light detector. Finally, while the above-described approach may assist in providing proper alignment, it does not allow one to verify that the alignment is, in fact, optimum or even acceptable after the sensor has been installed.

SUMMARY OF THE INVENTION

The inventive system for aligning a light source with a light detector in a pulse oximetry sensor may be either an integral part of a pulse oximetry monitor or a system used with a separate pulse oximetry monitor. The alignment system includes a light driver connected to the light source to energize the light source, and a receiver circuit connected to the light detector to generate an indicator signal corresponding to the magnitude of the light transmitted from the light source to the light detector. The receiver circuit is connected to a display which provides a visual indication of the magnitude of the indicator signal. As a result, the display can be monitored while the pulse oximetry sensor is being attached to a patient to optimize the alignment between the light source and the light detector.

The display preferably includes a bar graph on which the magnitude of the indicator signal is displayed. A threshold marking may be placed on the bar graph at a position corresponding to the magnitude of the indicator signal at which the light transmitted from the light source to the light detector falls to an unacceptable level. The threshold marking can then be used to set an alarm limit by comparing the indicator signal to a predetermined reference value, and generating an alarm signal when the magnitude of the indicator signal has fallen below the reference value. The alarm signal can then trigger an audible or visible alarm such as, for example, by flashing at least a portion of the bar graph when the light transmitted from the light source to the light detector fails below the acceptable level.

BRIEF DESCRIPTION OF THE DRAWINGS

FIG. 1 is an isometric view of a typical transmissive pulse oximetry sensor of the type in which the LED's and the light detector are mounted on a common flexible web.

FIG. 2 is a cross-sectional view taken along the line 2—2 of FIG. 1.

DETAILED DESCRIPTION OF THE INVENTION

Figure 3:
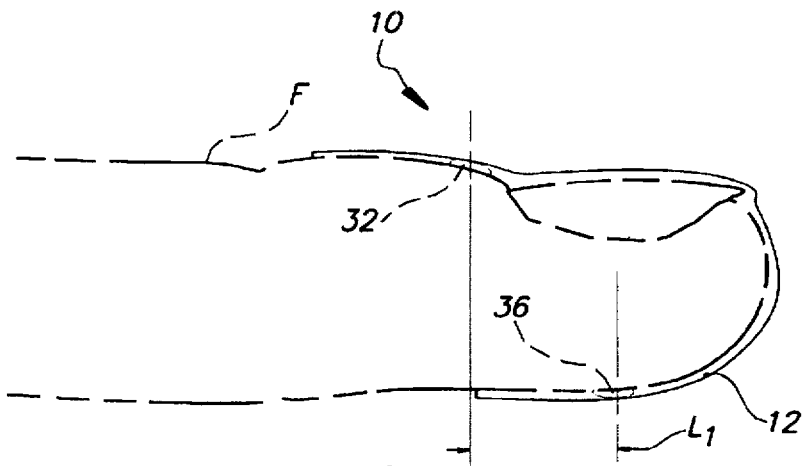
FIG. 3 is a cross-sectional view showing the pulse oximetry sensor of FIG. 1 applied with a lateral misalignment.

A conventional transmissive pulse oximetry sensor 10 of the type that can be used with the inventive alignment system is illustrated in FIGS. 1 and 2. The sensor 10 includes an elongated web 12 of flexible material, such as a woven fabric. One surface 14 of the web 12 is coated with a conventional adhesive 16 so that the web will stick to the skin of a patient and to the opposite surface 18 of the web 12 if the web 12 is wrapped around itself.

As illustrated in FIG. 2, a retention sheet 30 is secured to the adhesive surface 14 at one end of the web 12. A pair of light emitting diodes ("LED's") 32 mounted on a common substrate are sandwiched between the retention sheet 30 and the web 12 beneath a first transparent window 34 formed in the retention sheet 30. Similarly, a conventional light detector 36 is sandwiched between the retention sheet 30 and the web 12 beneath a second transparent window 38 formed in the retention sheet 30. The LED's 32 and light detector 36 are longitudinally spaced apart from each other by a distance that allows the LED's 32 and light detector 36 to directly face each other when the web 12 is doubled over and attached to the skin of the patient on opposite surfaces of a body part, such as a finger.

The LED's 32 and the light detector 36 are connected to respective wires, indicated generally at 40, which are bundled together to form a cable 42 that terminates in an electrical connector 44. The connector 44 plugs into a conventional pulse oximetry monitor (not shown in FIG. 1) to determine and display the oxygen saturation of vascularized tissues positioned between the LED's 32 and the light detector 36.

The sensor 10 is normally shipped and stored with the adhesive surface 14 of the web 12 attached to a release sheet 46 of plastic or the like having properties that allow the adhesive to easily separate from the sheet 46. When the sensor 10 is to be used, the release sheet 46 is stripped from the web 12, and the web 12 is attached to a body part, such as a finger, toe, hand, etc. of a patient, by forcing the adhesive surface 14 against the skin of the patient. As mentioned above, the web 12 should be attached so that the LED's 32 are positioned opposite and directly face the light sensor 36.

In an attempt to facilitate proper alignment between the LED's 32 and the light detector 36, alignment marks 50, 52, 54 are placed on the exposed surface 18 opposite the adhesive surface 14 as illustrated in FIG. 1. The first alignment mark 50 consists of a solid transverse line passing directly over the center of the LED's 32 with a circle at the center of the web 12 overlying the LED's 32. Similarly, the third alignment mark 54 consists of a solid transverse line passing directly over the center of the light detector 36 with a circle at the center of the web 12 overlying the light detector 36. Finally, the second alignment mark 52 consists of a dotted transverse line positioned midway between the first alignment mark 50 and the third alignment mark 54.

The alignment marks 50-54 attempt to assist the medical practitioner in applying the sensor 10 because the circles in the alignment marks 50, 54 should be directly opposite each other when the sensor 10 is properly attached. When the alignment marks 50, 54 are placed on opposite surfaces of a finger, toe, or hand, for example, the dotted alignment mark 52 should extend along the side of the finger, toe, or hand. However, in practice, these alignment marks 50-54 are often not effective in assisting medical practitioners in properly attaching the sensor 10 for the reasons explained below with reference to FIGS. 3-5.

One type of potential misalignment of the pulse oximetry sensor 10 of FIGS. 1 and 2 is illustrated in FIG. 3. As illustrated in FIG. 3, the web 12 is wrapped around the finger F of a patient. However, the web 12 is wrapped in a slight spiral configuration. As a result, the LED's 32 on the top of the finger F do not directly overly the light detector 36 on the bottom of the finger F. Instead, the LED's 32 and light detector 36 are displaced from each other by a distance $L_1$ along an axis extending laterally with respect to the web 12. Under these circumstances, the amount of light transmitted from the LED's 32 to the light detector 36 may be insufficient to provide highly accurate measurements of oxygen saturation.

It should be noted that the alignment marks 50–54 on the web 12 are incapable of preventing lateral misalignments of the type shown in FIG. 3 because the marks 50–54 are covered by the portion of the web 12 extending beyond the retention sheet 30. In fact, the portion of the web 12 containing the LED's 32 and the light detector 36 is covered by the extended portion of the web 12, thus making it virtually impossible to visually detect lateral misalignments.

Figure 4:
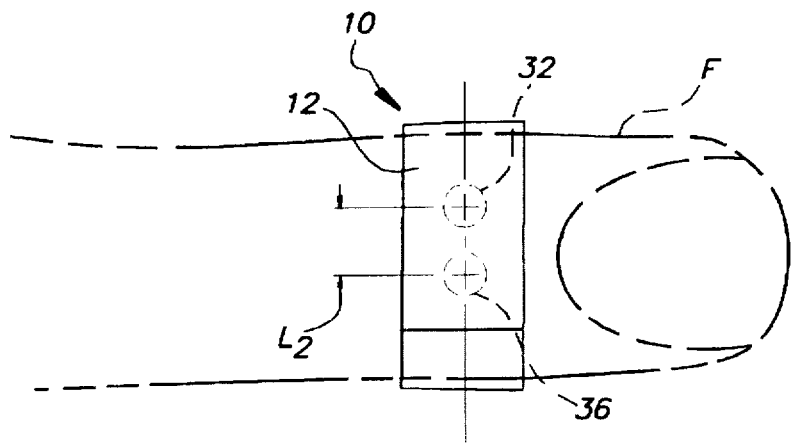
FIG. 4 is a cross-sectional view showing the pulse oximetry sensor of FIG. 1 applied with a longitudinal misalignment.

Another type of potential misalignment of the pulse oximetry sensor 10 of FIGS. 1 and 2 is illustrated in FIG. 4. As illustrated in FIG. 4, the web 12 is wrapped around the finger F of a patient. However, the LED's 32 are mounted on the web 12 at a distance from the light detector 36 that is different from one-half the circumference of the finger F. As a result, the LED's 32 on the top of the finger F do not directly overly the light detector 36 on the bottom of the finger F. Instead, the LED's 32 and light detector 36 are displaced from each other by a distance $L_2$ along an axis extending along the length of the web 12. Under these circumstances, the mount of light transmitted from the LED's 32 to the light detector 36 may also be insufficient to provide highly accurate measurements of oxygen saturation.

As with lateral misalignment of the type illustrated in FIG. 3, the alignment marks 50–54 on the web 12 are also incapable of preventing longitudinal misalignments of the type shown in FIG. 4 because it generally will not be possible to view both alignment marks 50 and 54 at the same time since they are on opposite surfaces of the finger F. Moreover in many application, including the application shown in FIG. 3, the alignment marks 50–54 will be covered by the portion of the web 12 extending beyond the retention sheet 30.

Figure 5:
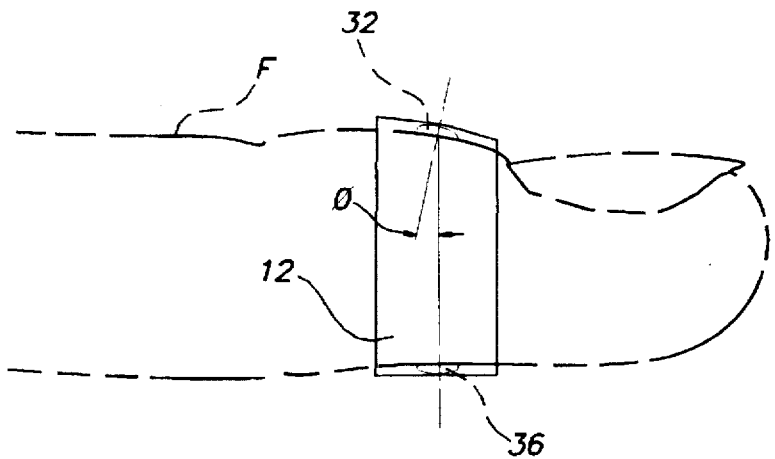
FIG. 5 is a cross-sectional view showing the pulse oximetry sensor of FIG. 1 applied with an angular misalignment.

Still another type of potential misalignment of the pulse oximetry sensor 10 of FIG. 1 is illustrated in FIG. 5. As illustrated in FIG. 5, the web 12 is wrapped around a portion of the finger F of a patient in which the opposite surface of the finger F are not parallel to each other. As a result, the LED's 32 on the top of the finger F do not directly face the light detector 36 on the bottom of the finger F. Instead, the illumination axes of the LED's 32 and the axis of sensitivity of the light detector 36 are displaced from each other by an angle θ. This angular misalignment may prevent the amount of light transmitted from the LED's 32 to the light detector 36 from being sufficient to provide highly accurate measurements of oxygen saturation, particularly where the illumination axes of the LED's 32 and the axis of sensitivity of the light detector 36 are relatively narrow.

The alignment marks 50–54 on the web 12 are also incapable of preventing angular misalignments of the type shown in FIG. 5 because it generally will not be possible to view both alignment marks 50 and 54 at the same time even if the marks 50–54 were not covered by the extended portion of the web 12. Also, it would be difficult to verify visually that the circle portions of the alignment marks 50, 54 are sufficiently parallel to each other.

Figure 6:
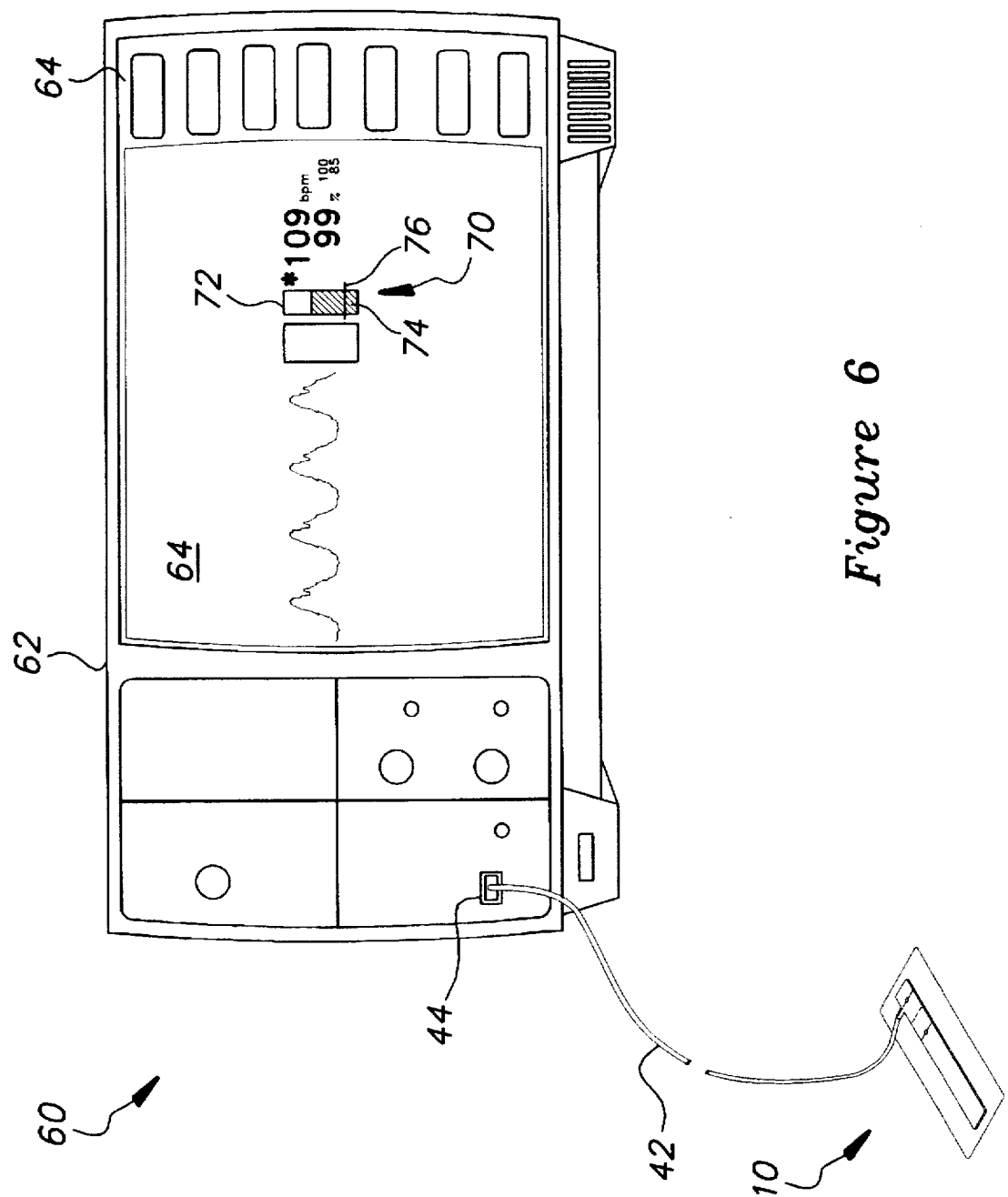
FIG. 6 is a cross-sectional view of a pulse oximetry system in which a pulse oximetry monitor using one embodiment of the inventive aiming guide system is connected to the pulse oximetry sensor of FIG. 1.

One embodiment of a pulse oximetry system 60 employing the inventive alignment system is illustrated in FIG. 6.

The pulse oximetry system 60 includes the transmissive pulse oximetry sensor 10 illustrated in FIGS. 1 and 2 connected to a pulse oximetry monitor 62 having a cathode ray tube screen 64. The monitor 62 illustrated in FIG. 6 is of the type using "softkeys" and a "touch screen" to control its operation. In monitors of this type, the "keys" are generated on the face of the screen by conventional software in the monitor 62, and the selection of a "key" is detected by a set of LED's (not shown) and light detectors (not shown) mounted on opposite sides of a bezel 66 surrounding the screen 64.

The monitor 62 employing the inventive alignment system departs from the prior art by adding to the screen 64 an alignment guide display. More specifically, a portion of the screen 64 contains a rectangular bar graph 70 defined by a rectangular outline 72 of fixed dimensions. The outline 72 is partially filled with an illuminated area 74. The height of the illuminated area 74 is a function of the magnitude of the light transmitted from the LED's 32 to the light detector 36. As a result, when the pulse oximetry sensor 10 is being attached to a patient, the height of the illuminated are 74 will provide the medical practitioner attaching the sensor 10 with feedback about amount of light being transmitted from the LED's 32 to the light detector 36. The position of the web 12 can then be adjusted to maximize the height of the illuminated area 74, thus optimizing the accuracy of the pulse oximetry system 60. It will be apparent to one skilled in the art that other types of graphical displays as well as numeric readouts could also be used without departing from the invention.

The bar graph 70 may simply display the degree of optical coupling between the LED's 32 and the light detector 36, or it may include an alarm for indicating that the optical coupling between the LED's 32 and the light detector 36 is insufficient to ensure accurate measurements. One type of alarm illustrated in FIG. 6 uses a solid line 76 extending across the bar graph outline 72 at a height corresponding to a predetermined optical coupling between the LED's 32 and the light detector 36. The predetermined optical coupling represented by the line 76 preferably corresponds to the point where the optical coupling falls to a level that is insufficient to obtain oxygen saturation measurements having more than a predetermined degree of accuracy. However, the line 76 may be set at any level depending upon the degree of misalignment that is to be permitted. When the illuminated area 74 drops below the level of the line 76, the entire bar graph 70 flashes off and on to alert the practitioner that the position of the pulse oximetry sensor 10 should be adjusted. Other types of alarms, including flashing lights, audible alarms, etc., could also be used.

Figure 7:
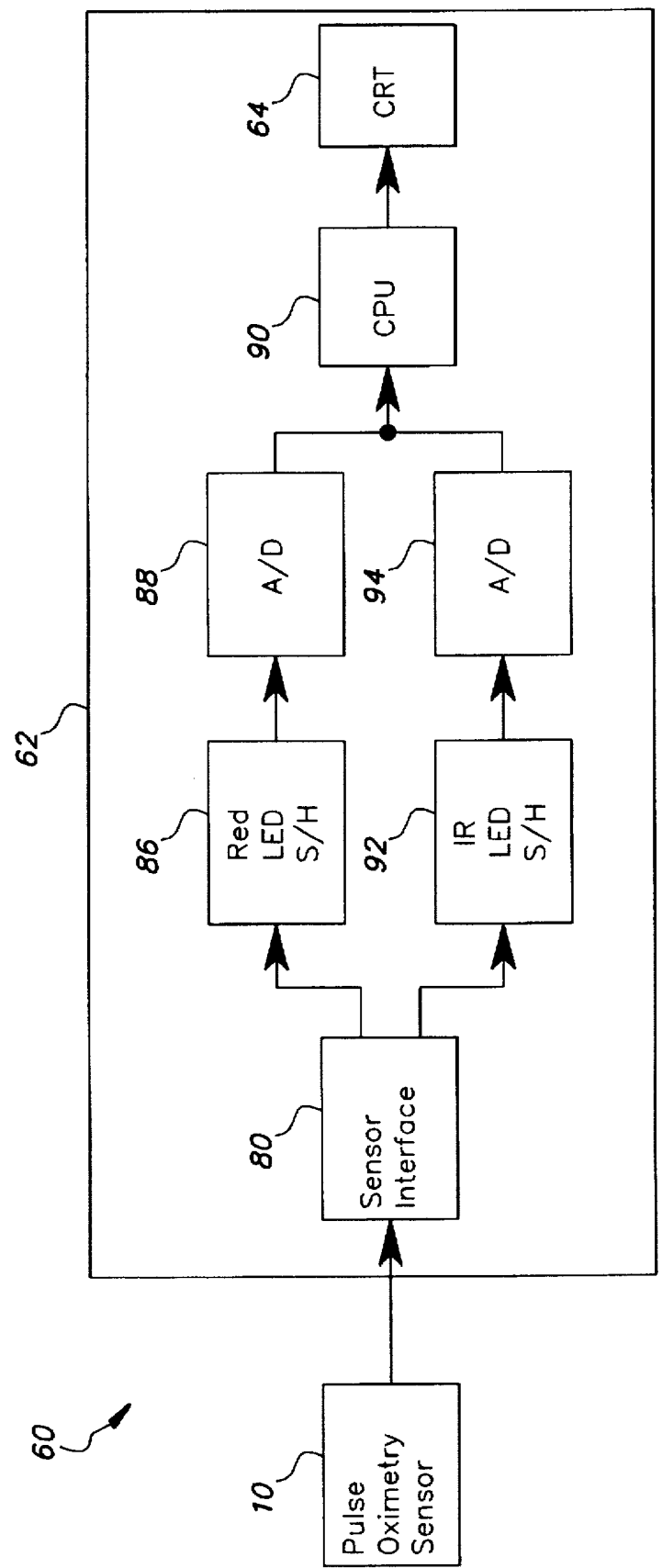
FIG. 7 is a block diagram of the pulse oximetry monitor of FIG. 6.

A block diagram of the pulse oximetry system 60 using the monitor 62 of FIG. 6 is illustrated in FIG. 7. It should be recognized that the portion of the monitor 62 that drives the LED's 32, processes the signal output by the light detector 36, calculates oxygen saturation, and displays the result is conventional. Thus, in the interest of brevity, these aspects of the monitor 62 are not described in detail herein.

The monitor 62 includes a sensor interface circuit 80 of conventional design that alternately pulses the LED's 32 (FIGS. 1 and 2) in the sensor 10 to cause the LED's 32 to alternately emit red and infra-red light. The light passes through vascularized tissues to the light detector 36 thereby causing the light detector 36 to output an indicator signal that is a function of the magnitude of the light transmitted through the tissues. The indicator signal is then amplified by the interface circuit 80 and directed to one of two outputs 82, 84 depending upon which LED 32 is illuminated when the indicator signal is received.

The indicator signal corresponding to the transmission of light from the red LED to the light detector 36 is applied from the output 82 to a first sample and hold ("S/H") circuit 86 of conventional design which periodically outputs analog samples. Each of these analog samples is a voltage corresponding to the amplitude of the red indicator signal from the interface circuit 80 when the sample was taken. The analog samples generated by the S/H circuit 86 are then converted to a digital value corresponding to the voltage of each sample by a conventional analog-to-digital ("A/D") converter 88. The resulting digital value indicative of the transmission of red light from the LED 32 to the light detector 36 is applied to an input port of a conventional microprocessor 90.

The indicator signal corresponding to the transmission of light from the infra-red LED to the light detector 36 is processed by similar circuitry. Specifically, the infra-red indicator signal is applied from the output 84 of the sensor interface circuit 80 to a second S/H circuit 92. Each of the analog samples generated by the S/H circuit 92 is then converted to a corresponding digital value by a second A/D converter 94. The resulting digital value indicative of the transmission of infra-red light from the LED 32 to the light detector 36 is applied to a second input port of the microprocessor 90.

The microprocessor 90 calculates the oxygen saturation of the patient from the red and infra-red digital samples in a conventional manner using the familiar Lambert-Beers equation. The result of the calculation is then displayed on the face of the cathode ray tube screen 64 (FIG. 6) in a known manner.

Figure 8:
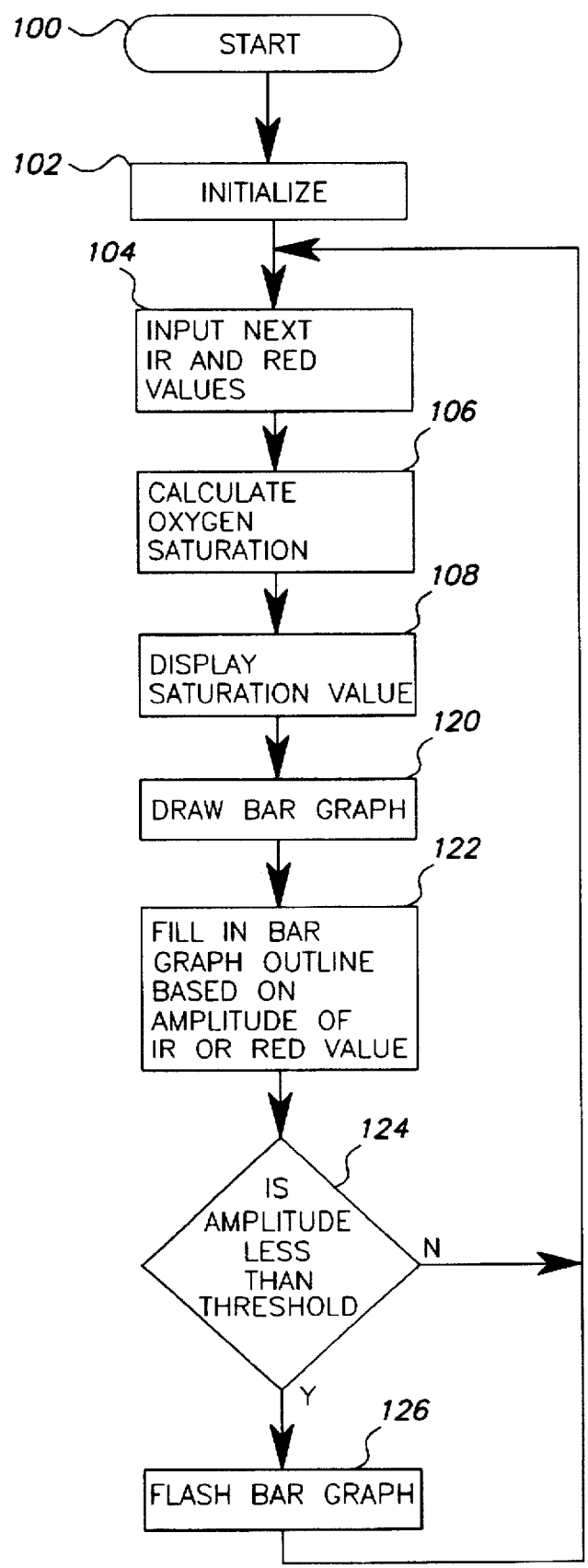
FIG. 8 is a flow chart of the software used to program a microprocessor used in the pulse oximetry monitor of FIGS. 6 and 7.

The microprocessor 90 operates according to a program of instructions that are stored in memory that is internal to the microprocessor 90. A flow chart showing this program from which one skilled in the art can easily and quickly write source code for a selected microprocessor type is illustrated in FIG. 8. It should be noted that the flow chart of FIG. 8 does not show the software in substantial detail for performing pulse oximetry functions, such as illuminating the LED's, calculating oxygen saturation, driving the CRT screen 64, etc. Such software is well known to one skilled in the art of pulse oximetry design since such software is used in a number of commercially available pulse oximetry monitors.

The program illustrated in FIG. 8 is entered at power on through step 100, and conventional initialization of flags, registers, etc. occurs at 102. The program then causes the microprocessor 90 (FIG. 7) to read the digitized red and infra-red samples from the A/D converters 88, 94 at step 104. The microprocessor 90 calculates oxygen saturation from these red and infra-red samples in a conventional manner at 106, and displays the calculated value on the CRT screen 64 at 108. The microprocessor 90 may also display the calculated value on the CRT screen 64 in graphical as well as numerical formats. For example, the microprocessor 90 may draw a running graph on the CRT screen 64 showing oxygen saturation as a function of time.

After the oxygen saturation value has been displayed the program executes a number of steps that implement the inventive alignment guide function. Step 120 of the program causes the microprocessor 90 to draw the rectangular outline 70 (FIG. 6) of the bar graph 70 as well as the solid line 76 designating the alarm limit threshold described above with reference to FIG. 6.

The program then progresses to step 122 where the microprocessor 90 fills in the outline 72 to form the illuminated area 74 depending upon the magnitude of either the digitized red sample generated by the A/D converter 88 or the digitized infra-red sample generated by the A/D converter 94. Although not necessary, a combination of both the red sample and the infra-red sample could also be used.

Regardless of whether the red sample, the infra-red sample, or some combination of both samples is used to set the height of the illuminated area 74, the value corresponding to the height of the illuminated area 74 is compared to the alarm limit threshold represented by the solid line 76 at step 124. If the program determines at step 124 that the sample used to set the height of the illuminated area 74 is less than the alarm limit threshold, the program causes the microprocessor 90 to flash the bar graph 70 at step 126. The program then returns to step 104 to obtain new red and infra-red samples. If the program determines at step 124 that the sample used to set the height of the illuminated area 74 is not less than the alarm limit threshold, the program returns directly to step 104 without passing through step 126 to flash the bar graph 70. The program continues to execute steps 104–126, thereby continuously displaying in essentially real time both the level of oxygen saturation as well as a guide for properly attaching the pulse oximetry sensor 10.

The inventive alignment guide system thus easily and quickly allows medical practitioners to properly attach transmissive pulse oximeter sensors as well as allowing them to monitor the correctness of the attachment during use. Furthermore, the alignment guide system may be used with virtually any type of conventional pulse oximetry monitor connected to such transmissive pulse oximeter sensors.

I claim:

1. A system for optimally positioning a light source with respect to a light detector in a plethysmograph sensor, said system comprising:
   a light driver connected to said light source to energize said light source, thereby causing said light source to emit light;
   a receiver circuit connected to said light detector, said receiver circuit generating an indicator signal that is indicative of the magnitude of the light transmitted from said light source to said light detector; and
   a display operably connected to said receiver circuit, said display providing a visual display of the magnitude of the light transmitted from said light source to said light detector as indicated by said indicator signal so that said display can be monitored while said plethysmograph sensor is being attached to a patient in order to optimize the positioning of said light source with respect to said light detector.

2. The system of claim 1 wherein said display includes a bar graph on which the magnitude of said indicator signal is displayed as a function of a dimension of said bar graph.

3. The system of claim 2 wherein said bar graph contains a threshold marking at a position on said bar graph corresponding to the magnitude of said indicator signal at which the light transmitted from said light source to said light detector falls below an acceptable level.

4. The system of claim 3 further including alarm means for signaling when the magnitude of said indicator signal shown on said bar graph has fallen below said threshold marking.

5. The system of claim 4 wherein said alarm means comprise:
   comparitor means for comparing said indicator signal to a predetermined reference value, said comparitor means providing an alarm signal when the magnitude of said indicator signal has fallen below said reference value; and alarm display means operatively coupled to said comparitor means and said display, said alarm display means flashing at least a portion of said bar graph responsive to said alarm signal thereby providing a visual indication when the light transmitted from said light source to said light detector falls below said acceptable level.

6. A pulse oximetry system, comprising:

a pulse oximetry sensor, comprising at least one light source and at least one light detector, said light sensor and said light detector being attachable to the skin of a patient so that said light detector and said light source can face each other; and a pulse oximetry monitor, comprising:

- a light driver connected to said light source to energize said light source, thereby causing said light source to emit light;
- a receiver circuit connected to said light detector, said receiver circuit generating first and second indicator signals that are indicative of the magnitude of the light transmissivity beneath said sensor at two different wavelengths, respectively; and
- a processor operatively connected to said receiver circuit, said processor receiving said first and second indicator signals, calculating the oxygen saturation of tissues beneath the skin of said patient to which said pulse oximetry sensor is attached, and generating a saturation signal corresponding the oxygen saturation of said tissues;
- a display operably connected to said processor and to said receiver circuit to receive said saturation signal and at least one of said indicator signals, said display providing a visual indication of the magnitude of the light transmitted from said light source to said light detector as indicated by said indicator signal received by said display so that said display can be monitored while said pulse oximetry sensor is being attached to said patient in order to optimize the positioning of said sensor, said display further providing a visual indication of the oxygen saturation of said tissues.

7. The pulse oximetry system of claim 6 wherein said display includes a bar graph on which the magnitude of said indicator signal is displayed as a function of a dimension of said bar graph.

8. The pulse oximetry system of claim 7 wherein said bar graph contains a threshold marking at a predetermined position on said bar graph corresponding to the magnitude of said indicator signal at which the light transmitted from said light source to said light detector fails to an unacceptable level.

9. The pulse oximetry system of claim 8 wherein said processor further includes alarm means for signaling when the magnitude of said indicator signal shown on said bar graph has fallen below said threshold marking.

10. The pulse oximetry system of claim 9 wherein said alarm means comprise:

comparitor means for comparing said indicator signal to a predetermined reference value, said comparitor means providing an alarm signal when the magnitude of said indicator signal has fallen below said reference value; and alarm display means operatively coupled to said comparitor means and said display, said alarm display means flashing at least a portion of said bar graph responsive to said alarm signal thereby providing a visual indication when the light transmitted from said light source to said light detector falls below said acceptable level.

11. The pulse oximetry system of claim 6 wherein said display includes a cathode ray tub screen which displays both a numerical value corresponding to the oxygen saturation of said tissues and an analog indication corresponding to the magnitude of the indicator signal received by said processor.

12. The pulse oximetry system of claim 6 wherein said display continuously provides a visual indication of the magnitude of the indicator signal received by said processor while a visual indication of the oxygen saturation of said tissues is shown on said display.

13. A method of optimally positioning a light source with respect to a light detector in a plethysmograph sensor, said system comprising:

(a) placing said plethysmograph sensor on a patient;

(b) measuring the magnitude of light transmitted from said light source to said light detector and providing an indicating signal corresponding thereto;

(c) providing a visual indication of the magnitude of light transmitted from said light source to said light detector as indicated by said indicating signal; and (d) repeating steps (a)–(c) while viewing said visual indicator until the magnitude of light transmitted from said light source to said light detector reaches an acceptable level.

14. The method of claim 13 further including the step of comparing the magnitude of said indicating signal to the magnitude of said indicator signal at which the light transmitted from said light source to said light detector falls to an unacceptable level.

* * * * *

UNITED STATES PATENT AND TRADEMARK OFFICE
CERTIFICATE OF CORRECTION

PATENT NO.     : 5,680,857
DATED          : October 28, 1997
INVENTOR(S)    : Pelikan et al.

It is certified that error appears in the above identified patent and that said Letters Patent is hereby corrected as shown below:

In column 9, claim 8, line 49, after "detector" delete "fails" and substitute therefor -- falls --.

Signed and Sealed this

Twenty-third Day of June, 1998

Attest:

BRUCE LEHMAN

*Attesting Officer*     *Commissioner of Patents and Trademarks*